United States Patent
Senzaki et al.

(10) Patent No.: US 6,664,433 B1
(45) Date of Patent: Dec. 16, 2003

(54) PROCESS FOR THE PURIFICATION OF AROMATIC HYDROCARBONS AND PROCESS FOR THE PREPARATION OF HIGH-PURITY AROMATIC HYDROCARBONS

(75) Inventors: Toshihide Senzaki, Kitakyushu (JP); Takahiro Imamura, Kitakyushu (JP); Takeshi Takayama, Kitakyushu (JP); Katsuhide Noguchi, Kitakyushu (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/958,817

(22) PCT Filed: Apr. 17, 2000

(86) PCT No.: PCT/JP00/02798

§ 371 (c)(1),
(2), (4) Date: Oct. 15, 2001

(87) PCT Pub. No.: WO00/66521

PCT Pub. Date: Nov. 9, 2000

(30) Foreign Application Priority Data

Apr. 28, 1999 (JP) .............................................. 11/122671
Jun. 15, 1999 (JP) .............................................. 11/168374

(51) Int. Cl.$^7$ ................................................. C07C 7/05
(52) U.S. Cl. .................... 585/864; 585/808; 585/807
(58) Field of Search ................ 585/807, 808, 585/864

(56) References Cited

U.S. PATENT DOCUMENTS 4,098,838 A * 7/1978 Grigoleit et al. .............. 549/49

FOREIGN PATENT DOCUMENTS

| FR | A1-2277061 | | 1/1976 |
|---|---|---|---|
| JP | 56-152702 | | 11/1981 |
| JP | A60-163802 | | 8/1985 |
| JP | A61-145129 | | 7/1986 |
| JP | 62-056442 | | 3/1987 |
| JP | A2-11528 | | 1/1990 |
| JP | A2-157233 | | 6/1990 |
| JP | A4-327543 | | 11/1992 |
| JP | 10-204005 | | 8/1998 |
| SU | 1066977 | * | 1/1984 |

* cited by examiner

Primary Examiner—Thuan D. Dang
(74) Attorney, Agent, or Firm—Birch Stewart Kolasch & Birch LLP

(57) ABSTRACT

This invention provides a process for purifying to a high degree of purity aromatic hydrocarbons containing impurities which are difficult to separate by distillation such as sulfur compounds and nitrogen compounds. The process of this invention for purifying aromatic hydrocarbons comprises treating crude aromatic hydrocarbons with a formaldehyde or with a formaldehyde and a phenol in the presence of an acid catalyst to form oligomers, distilling or evaporating the reaction mixture thereby separating the unreacted aromatic hydrocarbons from the oligomers, and crystallizing or washing with an organic solvent the separated aromatic hydrocarbons. In case the target hydrocarbon is naphthalene, it is possible to prepare naphthalene which has a purity of 99.9999 wt % or more, emits little odor, and can be readily flavored by perfumes. Naphthalene of this quality is used to prepare an insecticide of excellent fragrance.

8 Claims, No Drawings

PROCESS FOR THE PURIFICATION OF AROMATIC HYDROCARBONS AND PROCESS FOR THE PREPARATION OF HIGH-PURITY AROMATIC HYDROCARBONS

This application is the national phase under 35 U.S.C. §371 of PCT International Application No. PCT/JP00/02798 which has an International filing date of Apr. 27, 2000, which designated the United States of America.

FIELD OF TECHNOLOGY

This invention relates to a process for purifying aromatic hydrocarbons containing impurities such as aromatic heterocyclic compounds to obtain purified aromatic hydrocarbons, for example, high-purity naphthalene, and, more particularly, to a process for preparing high-purity naphthalene with a less offensive odor and good flavoring quality.

BACKGROUND TECHNOLOGY

Aromatic hydrocarbons such as benzene, toluene, xylene, ethylbenzene, naphthalene, methylnaphthalene, anthracene, acenaphthene, and phenanthrene are obtained from coal tar- or petroleum-derived raw materials. As these raw materials contain a variety of compounds, they go through a step for separation such as extraction, distillation and crystallization before they are made into final products.

For example, naphthalene occurs relatively abundantly in the middle fraction (boiling approximately in the range 200–250° C.) of petroleum- and coal-derived oil and it is recovered from this fraction by distillation and the like. Typically, naphthalene is prepared from a coal source as follows: coal tar is distilled to take out the middle fraction, acidic and basic components such as phenol and quinoline are extracted, and the remainder is distilled further or crystallized to recover naphthalene. The product obtained in this manner is crude naphthalene with a purity of 95% or so.

Crude naphthalene is generally purified by distillation or crystallization and, in the case of the latter process, recrystallization or continuous crystallization is adopted (JP58-46322 (1983)A1). A process based on a combination of azeotropic distillation and crystallization is proposed in JP03-2128 (1991)B2. Naphthalene purified by the aforementioned processes has a purity of nearly 100% and is used as an insecticide; even in a case such as this, the product is desirably as little colored and odorous as possible. On the other hand, where naphthalene is used as a raw material in the synthesis of pharmaceuticals, it desirably contains as little sulfur compounds impurities as possible because sulfur compounds act as catalyst poison. The aforementioned middle oil fraction, however, is known to contain a large number of impurities boiling close to one another and it is extremely difficult to remove those impurities completely.

Commercially available aromatic hydrocarbons other than naphthalene are also known to contain impurities which boil at points near those of the aromatic hydrocarbons in question. Typical impurities are sulfur-containing aromatic heterocyclic compounds such as thiophene and benzothiophene and nitrogen-containing heterocyclic compounds such as pyridine, quinoline and isoquinoline. When such other aromatic hydrocarbons are used as chemical raw materials, the impurities contained therein often act as catalyst poisons and their maximal removal is desirable. The impurities are also known to be emitters of an offensive odor.

For this reason, a variety of processes for purification by hydrogenation such as hydrodesulfurization have been proposed and adopted. However, such a process requires a high-pressure reactor or incurs a high processing cost.

The specification of JP04-327543 (1992)A1 points out the problems associated with the conventional desulfurization processes and proposes a process for purifying aromatic hydrocarbons by desulfurization, feasible in a relatively simple apparatus at a high efficiency, which comprises adding olefins to an aromatic hydrocarbon oil, effecting polymerization in the presence of an acid catalyst, and removing the sulfur-containing polymerization products by distillation. This process faces a problem in the treatment of polymerization products.

There often appears a demand for a high-purity aromatic hydrocarbon with a purity of 99.5 wt % or more, preferably 99.9 wt % or more. For example, naphthalene is used as an insecticide; the so-called naphthalene odor is shunned in this use and a perfume is often added for flavoring. In the case of flavoring, naphthalene is required to be free of an offensive odor and have an exceptionally low content of odorous impurities.

Known processes for preparing high-purity naphthalene on a commercial scale include 1) a combination of distillation and crystallization, 2) a combination of hydrogenation, compression, clay treatment and distillation and 3) a combination of hydrogenation, distillation and crystallization. Process 1) cannot separate naphthalene from impurity benzothiophene because the two not only boil at points close to each other but also form a solid solution. Processes 2) and 3) yield tetralin as a by-product which is difficult to separate. Thus, none of the three processes gives a satisfactory product.

An object of this invention is to provide a process for purifying aromatic hydrocarbons which is feasible in a simple apparatus at a high efficiency. Another object of this invention is to provide highly purified aromatic hydrocarbons. A further object of this invention is to provide purified naphthalene which is free of an offensive odor and suitable for use as an insecticide after flavoring with a perfume. A still further object of this invention is to provide a highly efficient desulfurization process which employs a relatively simple apparatus and procedure.

DISCLOSURE OF THE INVENTION

The present inventors have conducted studies to solve the aforementioned problems, found that those impurities which are present in raw material aromatic hydrocarbons and difficult to separate by such operation as distillation and crystallization can be separated efficiently by turning the impurities into heavy matters and distilling them, and arrived at this invention.

This invention relates to a process for purifying an aromatic hydrocarbon which comprises treating an aromatic hydrocarbon containing impurities with an aldehyde selected from formaldehyde and compounds generating formaldehyde in the reaction system such as paraformaldehyde or with said aldehyde and a phenol in the presence of an acid catalyst to form oligomers and recovering the unreacted aromatic hydrocarbon from the reaction mixture by evaporation or distillation.

An aromatic hydrocarbon containing impurities to be used as feedstock in this invention is a monocyclic aromatic hydrocarbon such as benzene, toluene, xylene and ethylbenzene or a polycyclic aromatic hydrocarbon such as naphthalene, methylnaphthalene, anthracene, acenaphthene and fluorene, although a polycyclic aromatic hydrocarbon containing two to three rings is preferable. The feedstock may contain two kinds or more of aromatic hydrocarbons, but it is advisable to adjust the content of the hydrocarbon at 70 wt % or more, preferably at 90 wt % or more, in advance by distillation or the like.

Impurities are contained in commercially available aromatic hydrocarbons and the purifying process of this invention is effective for those compounds which are difficult to separate by distillation, for example, sulfur compounds and nitrogen compounds. Typical sulfur compounds are sulfur-containing heterocyclic aromatic compounds such as thiophene and benzothiophene and their methyl- or ethyl-substituted derivatives while typical nitrogen compounds are nitrogen-containing heterocyclic aromatic compounds such as pyridine, indole, quinoline, isoquinoline and carbazole and their methyl- or ethyl-substituted derivatives. Normally, sulfur compounds contain 100–10,000 wt ppm of sulfur while nitrogen compounds contain 10–5,000 wt ppm of nitrogen.

The feedstock aromatic hydrocarbon oil may contain aliphatic hydrocarbons and phenols, but it is better to remove bases and components harming the activity of a catalyst in advance. A suitable aromatic hydrocarbon is the one or a fraction containing it separated from petroleum or coal tar, preferably the one or a fraction thereof obtained from coal tar. For example, crude naphthalene or a naphthalene oil containing 10 wt % or more of naphthalene or methylnaphthalene is advantageous as feedstock.

In case the target is high-purity naphthalene, crude naphthalene to be used as feedstock is adjusted to have a purity of 80% or more, preferably 90% or more, and it does not matter whether it is derived from petroleum or coal tar. More preferable as feedstock is crude naphthalene which is referred to as "coal-derived 95% naphthalene." Crude naphthalene may contain a variety of aromatic hydrocarbons and phenols, but bases such as quinoline are desirably removed, for example, by washing with an acid because they act as catalyst poisons. However, these bases are difficult to remove completely and they may be left in at such a level as not to interfere significantly with the catalytic reaction. Although there is no restriction on the impurities present in crude naphthalene, the process is effective for ordinary crude naphthalene containing methylbenzonitriles, dimethylbenzonitriles, dimethylanlines, benzothiophene, tetralin, trimethylphenols and quinoline as principal impurities.

An aldehyde to be used in this invention can be any compound which generates formaldehyde in the reaction system and formaldehyde itself, formalin or paraformaldehyde can be used as such, the last being favorable.

A phenol can be used together with an aldehyde in this invention and useful phenols include phenol, alkylphenols such as cresol, xylenol and t-butylphenol, polyhydric phenols such as resorcin and pyrogallol and hydroxylated polycyclic aromatic compounds such as naphthol. It is desirable, however, to use a monohydric phenol such as phenol and an alkylphenol from the standpoint of reactivity and utilization of by-product oligomers.

Acid catalysts useful for this invention include inorganic acids such as sulfuric acid, phosphoric acid and hydrochloric acid, organic acids such as oxalic acid and toluenesulfonic acid, Lewis acids such as aluminum chloride and boron trifluoride and their complexes, and solid acids such as silica-alumina, zeolites, ion exchange resins and acid clay. Preferable among them are organic acids such as oxalic acid and toluenesulfonic acid. A thermally decomposable catalyst such as oxalic acid has an additional merit that a procedure for its removal can be omitted.

The proportion of an aldehyde or phenols to the crude aromatic hydrocarbon feedstock varies with the properties of feedstock such as purity and, suitably, the aldehyde (computed as formaldehyde) is in the range 10–50 parts by weight, preferably 20–40 parts by weight, and the phenols is in the range 0–70 parts by weight, preferably 30–60 parts by weight, per 100 parts by weight of the crude aromatic hydrocarbon. Too much aldehyde raises the conversion of the aromatic hydrocarbon thereby decreasing the yield of the aromatic hydrocarbon while too little aldehyde leaves more of the impurities unreacted. Phenols are more reactive than aromatic hydrocarbons and they act to lower the conversion of aromatic hydrocarbons and besides improve the properties of by-product oligomers. It may be advantageous not to use the phenols, however, in case oligomers of not too high molecular weight or oligomers free of phenols units are desired from the standpoint of utilization of oligomers.

The amount of an acid catalyst, although varying with the kind of catalyst, is generally 0.5–20 wt % of the reactants and it is 5–10 wt % in the case of oxalic acid.

The reaction conditions vary with the feedstock and catalyst in use and, in general, the reaction temperature is 50–180° C. and the reaction time is 0.5–5 hours. In this reaction, an aromatic hydrocarbon, impurities and an aldehyde participate in the reaction to form oligomers such as aromatic hydrocarbon resins. In case a phenol is added to the reaction system, the reaction products are oligomers such as aromatic hydrocarbon-modified novolak resins or phenol-modified hydrocarbon resins. It is desirable to carry out the reaction in such a manner as to exhaust all of the reactive components other than the aromatic hydrocarbon and to keep the conversion of the aromatic hydrocarbon at 50% or less, preferably at 5–30%.

In case the aromatic hydrocarbon feedstock is naphthalene, naphthalene, impurities in naphthalene, and the aldehyde participate in the reaction to form oligomers such as naphthalene-based hydrocarbon resins. In case a phenol is added to the reaction system, the reaction will yield oligomers such as naphthalene-modified novolak resins or phenol-modified hydrocarbon resins. It is preferable to allow components other than naphthalene to react as much as possible and keep the conversion of naphthalene at 10–50%.

Although aromatic hydrocarbons participate in this reaction, those impurities which contain heteroatoms react relatively preferentially. Therefore, it is possible to raise the conversion of impurities such as benzothiophene to 90–99% if the conversion of aromatic hydrocarbons is kept at 10% or more.

A solvent is used in case the crude aromatic hydrocarbon feedstock is solid at the reaction temperature or, if necessary, even in case the feedstock is liquid.

After completion of the reaction, the reaction mixture is distilled to strip off water and low-boiling substances such as formaldehyde and then heated to 200–300° C. or above under reduced pressure to distill the aromatic hydrocarbon. Depending upon the conditions for distillation and the purity of the feedstock, it is possible to obtain a fraction containing 99% or more of the aromatic hydrocarbon practically free of sulfur compounds. The purity can be raised further, if necessary, by submitting the material to crystallization or to washing and/or precise fractional distillation.

The residue is oligomers and can be used as hydrocarbon resins, modified novolak resins, or modified hydrocarbon resins. Upon completion of the reaction, the catalyst may be removed by such a procedure as washing with water and the reaction terminates at this point. Without removal of the catalyst, the reaction partially progresses during distillation.

In the case where crystallization is performed, a procedure of either continuous crystallization or recrystallization is followed, though recrystallization is simpler of the two. For example, in case the target aromatic hydrocarbon is naphthalene, a low-boiling organic solvent such as methanol, ethanol and acetone is used as a solvent for recrystallization. Methanol as a solvent is generally used at a rate of 2–6 parts by weight per 1 part by weight of naphthalene and the naphthalene is dissolved by heating at 50–70° C. and precipitated by cooling the solution to 20–0° C. It is usually sufficient to perform recrystallization once and, if necessary, recrystallization can be repeated twice or more times. As for washing, an organic solvent such as methanol is used in an amount insufficient to dissolve the naphthalene in whole and the naphthalene is agitated with the solvent and submitted to a treatment such as solid-liquid separation.

The purified aromatic hydrocarbon obtained in this manner can attain a purity of 99.99 wt % or more. In case it is naphthalene, it has a purity of 99.99 wt % or more and, if the content of quinoline is reduced to below 10 wt ppm, shows a markedly reduced emission of odor compared with the conventionally purified naphthalene. Moreover, if the content of quinoline in purified naphthalene is below 1.0 wt ppm, odor is nearly absent and the human organ of smell cannot detect it. Naphthalene of this quality not only does not emit an offensive odor or the so-called naphthalene odor but also can be readily flavored when a perfume is incorporated. The amount of a perfume to be incorporated is 1 wt % or less, preferably 0.01–0.1 wt %. Useful perfumes include oils extracted from natural sources such as rose oil and herb oil and synthetic materials.

The aforementioned product qualities improve further if each of organic impurities other than quinoline in purified naphthalene is kept below 1.0 wt ppm. Purified naphthalene exhibiting a purity of 99.9999 wt % or more and containing less than 1.0 wt ppm each of quinoline and organic impurities other than quinoline is a commercial novelty and it has not been used as an insecticide. If used as such, this novel product imperceptibly emits the so-called naphthalene odor and the odor soaks into clothing with difficulty. Moreover, it is possible to flavor the novel product with a perfume and let only the fragrance persist. The aforementioned ultra-high-purity naphthalene can be prepared easily by the purifying process of this invention, but the process is not limited to this particular one. For example, purified naphthalene such as this can be prepared easily by carrying out the aforementioned reaction and distillation and performing recrystallization once or twice. In the determination and calculation of the purity described above, the impurities refer to organic compounds contained in crude naphthalene with no account taken for any components present in air such as moisture and the purity of naphthalene is calculated by substracting the concentration of impurities from 100%. The limit of determination of the impurities is below 1 wt ppm.

PREFERRED EMBODIMENTS OF THE INVENTION

This invention will be described below with reference to examples. In the examples, %, ppm and parts are all on a weight basis.

EXAMPLE 1

To a flask were added 134 parts of coal-derived 95% naphthalene (consisting of 0.07% of methylbenzonitriles, 1.6% of benzothiophene, 0.02% of tetralin, 0.07% of trimethylphenols, and 0.09% of quinoline), 68 parts of p-tertiarybutylphenol and 34 parts of 98% paraformaldehyde, the mixture was maintained at 110° C., and 22 parts of oxalic acid was added to the mixture. The whole mixture was allowed to react at 130° C. with stirring for 2.5 hours to yield oligomers. Low-boiling substances such as water being formed were refluxed.

Upon completion of the reaction, a condenser was attached to the flask and the reaction mixture was distilled at atmospheric pressure. Low-boiling substances such as water and formaldehyde were distilled off by the time the temperature reached 200° C. Then, the distillation was carried out under reduced pressure at 100 mmHg while raising the temperature from 200° C. to 270° C. to collect 100 parts of a naphthalene fraction with a purity of 99.9% or more. The resins remaining in the flask were washed with water and the catalyst was removed to give 120 parts of oligomers with a softening point of 113.6° C.

To 400 parts of methanol was added 100 parts of the naphthalene fraction, the fraction was dissolved completely at 60° C., the solution was cooled to 10° C. to precipitate crystals, and the mixture was submitted to solid-liquid separation. The purified naphthalene separated as solid amounted to 75 parts and it was 99.999% pure with the total of impurities detectable by gas chromatography amounting to 10 ppm or less. Of the impurities, methylbenzonitriles, dimethylbenzonitriles, dimethylanilines, benzothiophene, tetralin, and trimethylphenols were not detected and 9 ppm of quinoline was present. Organoleptic test indicated that the purified naphthalene was practically free of an offensive odor and exhibited a good quality for incorporation of perfumes.

To 300 parts of methanol was added 75 parts of the purified naphthalene, the fraction was dissolved completely at 60° C., the solution was cooled to 10° C. to precipitate crystals, and the mixture was submitted to solid-liquid separation. The purified naphthalene separated as solid amounted to 50 parts and its purity was 99.9999% with the total of impurities detectable by gas chromatography amounting to 1 ppm or less. None of methylbenzonitriles, dimethylbenzonitriles, dimethylanilines, benzothiophene, tetralin, trimethylphenols and quinoline was detected (below 1 ppm). Organoleptic test indicated that the odor of the purified naphthalene was reduced further and was imperceptible in the test.

EXAMPLE 2

To 500 parts of methanol was added 100 parts of the naphthalene fraction obtained in Example 1, the fraction was dissolved completely at 60° C., the solution was cooled to 10° C. to precipitate crystals, and the mixture was submitted to solid-liquid separation. The purified naphthalene separated as solid amounted to 45 parts and its purity was 99.9999% with the total of impurities detectable by gas chromatography amounting to 1 ppm or less. None of methylbenzonitriles, dimethylbenzonitriles, dimethylanilines, benzothiophene, tetralin, trimethylphenols and quinoline was detected (below 1 ppm). Organoleptic test indicated that the purified naphthalene emitted no perceptible odor.

EXAMPLE 3

To a flask were added 134 parts of coal-derived 95% naphthalene (containing sulfur compounds equivalent to 5,000 ppm as sulfur), 68 parts of p-tertiarybutylphenol and 10 parts of 98% paraformaldehyde, the mixture was maintained at 110° C., and 15 parts of oxalic acid was added to the mixture. The whole mixture was allowed to react at 130° C. with stirring for 2.5 hours to yield oligomers. Low-boiling substances such as water being formed were refluxed.

Upon completion of the reaction, a condenser was attached to the flask and the reaction mixture was distilled at atmospheric pressure. Low-boiling substances such as water and formaldehyde were distilled off by the time the temperature reached 200° C. Then, the distillation was carried out under reduced pressure at 100 mmHg while raising the temperature from 200° C. to 270° C. to collect a naphthalene fraction.

The naphthalene fraction amounted to 114 parts and the flask contained 100 parts of oligomers with a softening point of 113.6° C. The content of sulfur in the naphthalene fraction was 10 ppm as determined by ion chromatography and this indicates that 99% or more of sulfur has been removed.

The purity of the naphthalene fraction as determined by gas chromatography was 99.9% or more (the total content of methylbenzonitriles, dimethylbenzonitriles, dimethylanilines, benzothiophene, tetralin and trimethylphenols was 50 ppm or less and the content of quinoline was 150 ppm).

EXAMPLE 4

To a flask were added 176 parts of a mixture of coal-derived methylnaphthalenes (containing sulfur compounds equivalent to 5,200 ppm as sulfur), 80 parts of p-tertiarybutylphenol and 44 parts of 98% paraformaldehyde, the mixture was maintained at 110° C., and 23 parts of oxalic acid was added to the mixture. The whole mixture was allowed to react at 130° C. with stirring for 2.5 hours to yield oligomers. Low-boiling substances such as water being formed were refluxed.

Upon completion of the reaction, a condenser was attached to the flask and the reaction mixture was distilled at atmospheric pressure. Low-boiling substances such as water and formaldehyde were distilled off by the time the temperature reached 200° C. Then, the distillation was carried out under reduced pressure at 100 mmHg while raising the temperature from 200° C. to 270° C. to collect a methylnaphthalene fraction. The methylnaphthalene fraction amounted to 131 parts and the flask contained 139 parts of oligomers with a softening point of 140.7° C. The content of sulfur in the methylnaphthalene fraction was 200 ppm as determined by ion chromatography.

EXAMPLE 5

To a flask were added 310 parts of a coal-derived anthracene mixture (containing sulfur compounds equivalent to 6,000 ppm as sulfur), 106 parts of p-tertiarybutylphenol and 52 parts of 98% paraformaldehyde, the mixture was maintained at 110° C., and 28 parts of oxalic acid was added to the mixture. The whole mixture was allowed to react at 130° C. with stirring for 2.5 hours to yield oligomers. Low-boiling substances such as water being formed were refluxed.

Upon completion of the reaction, a condenser was attached to the flask and the reaction mixture was distilled at atmospheric pressure. Low-boiling substances such as water and formaldehyde were distilled off by the time the temperature reached 200° C. Then, the distillation was carried out under reduced pressure at 100 mmHg while raising the temperature from 200° C. to 280° C. to collect an anthracene fraction. The anthracene fraction amounted to 191 parts and the flask contained 235 parts of oligomers with a softening point of 105.0° C. The content of sulfur in the anthracene fraction was 250 ppm as determined by ion chromatography.

EXAMPLE 6

To a flask were added 1,152 parts of coal-derived 95% naphthalene (containing sulfur compounds equivalent to 5,000 ppm as sulfur) and 203 parts of 98% paraformaldehyde, the mixture was maintained at 110° C., and 134 parts of oxalic acid was added to the mixture. The whole mixture was allowed to react at 130° C. with stirring for 2.5 hours to yield oligomers. Low-boiling substances such as water being formed were refluxed.

Upon completion of the reaction, a condenser was attached to the flask and the reaction mixture was distilled at atmospheric pressure. Low-boiling substances such as water and formaldehyde were distilled off by the time the temperature reached 200° C. Then, the distillation was carried out under reduced pressure at 100 mmHg while raising the temperature from 200° C. to 270° C. to collect a naphthalene fraction. The naphthalene fraction amounted to 677 parts and its purity was 99.9% or more. The flask contained 434 parts of oligomers with a softening point of 56.5° C. The content of sulfur in the naphthalene fraction was 100 ppm as determined by ion chromatography.

EXAMPLE 7

To a flask were added 115 parts of coal-derived crude benzene (containing sulfur compounds equivalent to 2,000 ppm as sulfur) and 20 parts of 98% paraformaldehyde, the mixture was maintained at 80° C., and 13 parts of oxalic acid was added to the mixture. The whole mixture was allowed to react at 80° C. with stirring for 2.5 hours to yield oligomers.

Upon completion of the reaction, a condenser was attached to the flask and the reaction mixture was distilled at atmospheric pressure. Low-boiling substances such as water and formaldehyde were distilled off by the time the temperature reached 150° C. Then, the distillation was carried out under reduced pressure at 50 mmHg while raising the temperature from 150° C. to 200° C. to collect a benzene fraction. The benzene fraction amounted to 100 parts and the flask contained 20 parts of liquid oligomers. The content of sulfur in the benzene fraction was 100 ppm as determined by ion chromatography.

INDUSTRIAL APPLICABILITY

The process of this invention can purify aromatic hydrocarbons containing sulfur compounds impurities which are difficult to separate by distillation to a high degree of purity. Aromatic hydrocarbons obtained by the process of this invention are useful as chemicals such as insecticides or raw materials for pharmaceuticals because of extremely low contents of impurities such as sulfur compounds. In case the target hydrocarbon is naphthalene, it becomes possible to obtain easily a material of an exceptionally high purity (99.9999 wt %) with reduced emission of odor. Naphthalene of this quality can be flavored readily by perfumes and made into an insecticide of excellent fragrance. Moreover, by-product oligomers can be used as hydrocarbon resins, modified novolak resins or modified hydrocarbon resins.

What is claimed is:

1. A process for purifying an aromatic hydrocarbon comprising:

(i) treating an aromatic hydrocarbon containing impurities with an aldehyde selected from the group consisting of formaldehyde and compounds generating formaldehyde in a reaction system, and at least one phenol in the presence an acid catalyst to form oligomers, (ii) distilling or evaporating the mixture of (i) to separate unreacted aromatic hydrocarbon from oligomers, (iii) crystallizing the separated aromatic hydrocarbon, and optionally (iv) washing the crystallized aromatic hydrocarbon with an organic solvent;

wherein the proportion of the aldehyde is in the range of 20–40 parts by weight, and at least one phenol is in the range of 30–60 parts by weight, per 100 parts by weight of the aromatic hydrocarbon.

2. A process for preparing a purified aromatic hydrocarbon comprising:

(i) treating an aromatic hydrocarbon containing sulfur compounds as impurities with an aldehyde selected from the group consisting of formaldehyde and compounds generating formaldehyde in a reaction system, and at least one phenol in the presence of an acid aldehyde, to form oligomers, (ii) recovering unreacted aromatic hydrocarbon from the mixture of (i) by distillation, (iii) crystallizing the recovered aromatic hydrocarbon with an organic solvent; and optionally (iv) washing the crystallized aromatic hydrocarbon;

wherein the proportion of aldehyde is in the range of 20–40 parts by weight, and the proportion of at least one phenol is are in the range of 30–60 parts by weight, per 100 parts by weight of the aromatic hydrocarbon.

3. The process for preparing a purified aromatic hydrocarbon as described in claim 2 wherein the aromatic hydrocarbon containing sulfur compounds as impurities is naphthalene or a naphthalene oil containing heterocyclic sulfur compounds as impurities.

4. The process for preparing a purified aromatic hydrocarbon as described in claim 2 wherein the purified aromatic hydrocarbon is naphthalene.

5. The process for preparing a purified aromatic hydrocarbon as described in claim 2 wherein the purified aromatic hydrocarbon is naphthalene, and the purity of purified naphthalene is 99.99 wt % or more and the content of quinoline is below 10 wt ppm.

6. The process for preparing a purified aromatic hydrocarbon as described in claim 2 wherein the purified aromatic hydrocarbon is naphthalene, and the purity of purified naphthalene is 99.99 wt % or more and the content of quinoline is below 1.0 wt ppm.

7. The process for preparing a purified aromatic hydrocarbon as described in claim 2 wherein the purified aromatic hydrocarbon is naphthalene, and the purity of purified naphthalene is 99.99 wt % or more and the content of the quinoline is below 1.0 wt ppm and the content of each of organic impurities, other than quinoline in purified naphthalene, is below 1.0 wt ppm.

8. The process for preparing a purified aromatic hydrocarbon as described in claim 2 wherein the purified aromatic hydrocarbon is naphthalene, and the purity of purified naphthalene is 99.9999 wt % and contains less than 1.0 wt ppm of quinoline and less than 1.0 wt ppm each of organic impurities, other than quinoline.

* * * * *